(12) United States Patent
Bianco-Peled et al.

(10) Patent No.: US 8,673,354 B2
(45) Date of Patent: Mar. 18, 2014

(54) ADHESIVES AND METHODS OF APPLYING THE SAME

(75) Inventors: Havazelet Bianco-Peled, Haifa (IL); Ohad Kimhi, Kiryat Yam (IL)

(73) Assignee: Technion Research and Development Foundation Ltd., Haifa (IL)

( * ) Notice: Subject to any disclaimer, the term of this patent is extended or adjusted under 35 U.S.C. 154(b) by 290 days.

(21) Appl. No.: 12/741,515

(22) PCT Filed: Nov. 5, 2008

(86) PCT No.: PCT/IL2008/001452
§ 371 (c)(1),
(2), (4) Date: Sep. 13, 2010

(87) PCT Pub. No.: WO2009/060439
PCT Pub. Date: May 14, 2009

(65) Prior Publication Data
US 2011/0015125 A1    Jan. 20, 2011

Related U.S. Application Data

(60) Provisional application No. 60/985,349, filed on Nov. 5, 2007, provisional application No. 61/039,564, filed on Mar. 26, 2008.

(51) Int. Cl.
*A61K 9/14* (2006.01)
(52) U.S. Cl.
USPC ........................................ 424/484; 424/78.06

(58) Field of Classification Search
None
See application file for complete search history.

(56) References Cited

U.S. PATENT DOCUMENTS

2008/0295735 A1* 12/2008 Ragaru et al. .............. 106/124.4

FOREIGN PATENT DOCUMENTS

| GB | 2336156 A | * 10/1999 |
| WO | 97/41900 A1 | 11/1997 |
| WO | 2009/060438 A2 | 5/2009 |

OTHER PUBLICATIONS

Haslem et al., "Polyphenol Complexation, a Study in Molecular Recognition" American Chemical Society, 506:8-50 (1992).
Bitton et al., "The Influence of Halide-Mediated Oxidation on Algae-Born Adhesives" Macromol Biosci 7:1280-1289 (2007).

\* cited by examiner

*Primary Examiner* — Anand Desai
*Assistant Examiner* — Melissa Mercier
(74) *Attorney, Agent, or Firm* — Browdy and Neimark, PLLC

(57) ABSTRACT

A composition including pre-gel including at least one phenol-based compound, excluding phloroglucinol and derivatives, at least one water miscible polymer, at least one cross linking agent capable of interacting with the polymer. The polymer is selected from one or more natural and/or synthetic carbohydrate, and salt of an anionic polysaccharide.

21 Claims, 5 Drawing Sheets

Gallic acid

Morin

Naringenin

Epicatechin

Catechin

Epigallocatechin

Gallocatechin

Epigallocatechin gallate

Epicatechin gallate

ADHESIVES AND METHODS OF APPLYING THE SAME

FIELD OF THE INVENTION

The present invention relates to adhesives. More particularly, the present invention relates to adhesive composition of matter and methods of applying the same, especially in medical applications.

BACKGROUND OF THE INVENTION

Tissue adhesives have been increasingly used to enhance traditional closure technologies such as sutures and staples, offering improved sealing capabilities and plugging of undesired leaks[1]. However, despite recent developments and increased clinical demand, currently available products still suffer from serious drawbacks. While synthetic adhesives have low biocompatibility, low adherence to wet surfaces and potential toxicity, the biological glues are costly, often show relatively poor mechanical and tissue-bonding properties, and are potentially immunogenic, as most of them are based on proteins. Thus, there is a genuine unmet need for non-toxic, strong, and economical tissue sealants to sustain internal surgical incision closure, as an adjunct to suturing or stapling. This need was the main motivation for the development of bio-mimicking adhesives, which received increasing attention in the last decade.

Using an adhesive for tissue reattachments or repair procedures usually require the adhesive to be applied onto a hydrated tissue surface. Moreover, biomedical adhesives have to overcome contact with physiological fluids such as blood or saline in order to form contacts or associations with the underlying tissue. The success of synthetic adhesives in a hydrated environment is limited, and typically requires certain treatments and/or performing partial dehydration of the contact surface[2]. In contrast to synthetic materials, nature has very effectively conquered the limitations of sticking to wet surfaces[3]. Marine sessile organisms such as barnacles, reef worms, mussels, algae have life histories that depend on their secure attachment to solid substrate for survival. These organisms produce and secrete adhesives that form permanent, strong and flexible underwater bonds to virtually any hard surface[4]. For example, mussels attach to wet surfaces by creating a byssus, an extracorporeal bundle of tiny tendons that are attached distally to a foreign substratum and proximally by insertion of the stem root into the byssal retractor muscles. "Mussel glues" have been proposed to be suitable for medical applications due to their high adhesion strength and their ability to adhere to wet surfaces. However, it is clear that the commercial production of such glues is currently not practical, since extraction of 1 kg of the naturally existing adhesive raw materials (proteins and polypeptides) would require processing five to ten million mussels[1].

An alternative and more practical method is based on taking a 'biomimetic' approach, which entails constructing artificial materials that mimic natural forms. Polymeric analogs may be synthesized, as an example, from amino acids that were identified as being functional to naturally existing adhesive proteins. Much effort has been made to synthesize random block copolymers, which are biomimetic approximations of naturally existing adhesive proteins and polypeptides[2, 8-20].

Another effective natural adhesion mechanism exists in red and brown algae, which produce phenolic compounds that exhibit adhesive properties and extraordinarily high cohesive strength. These adhesive contain phenolic compounds that bind non-specifically to both hydrophobic and hydrophilic surfaces in aqueous conditions[21]. The secretion of these phenolic compounds is coupled with peroxidase oxidation and results in their crosslinking of cell-wall polysaccharides. Based on those observations, Vreeland et al. disclosed in U.S. Pat. No. 5,520,727 entitled "Aqueous algal-based phenolic type adhesives and glues" in which the algal-based phloroglucinol was activated and cross linked with algal carbohydrates in order to form glue. The inventors of the present invention have demonstrated that formulations composed of oxidized polyphenol extracted from *Fucus serratus*, alginate and calcium ions are capable of adhering to a variety of surfaces[23]. Structural analysis using small angle x-ray scattering (SAXS) and electron microscopy (cryo-TEM) showed that the polyphenols self-assemble into chain-like objects[24]. Oxidation did not alter this overall structure, causing only a reduction in the aggregate size. Moreover, this chain-like structure did not change upon addition of alginate. Once calcium ions were added, a network (whose overall structure resembled that of the alginate gel) was formed.

Since the production of nature-based glues such as disclosed in Vreeland et al. and others rely on extracting natural materials from tons of algae, there was a need to synthetically imitate the remarkable ability of marine algae to attach to wet solid surface in order to provide effective adhesives having characteristics that are similar to the characteristics of the marine algae.

Using the biomimetic approach, the inventors of the present invention hypothesized that the natural components of the "fucus glue" can be successfully replaced with commercially available analogue that provides similar functionally. In PCT/IL2006/000289, the inventors of the present invention indeed showed that the monomeric unit of phloroglucinol and several of its derivatives to interact with polysaccharide such as alginate to form an adhesive that was shown to adhere in various compositions to animal tissues as well as to other surfaces.

Interactions between carbohydrates and polyphenols are not unique to algae adhesives. Polyphenols are a large and very diverse family of plant metabolites, characterized by the presence of more than one phenol group per molecule[25-30].

It is needed to extend the adhesive composition beyond the biomimetic approach and to develop adhesive composition of matter that are able to form strong interactions with surfaces, whether dry or wet, as well as within the network itself.

Moreover, the method of applying the adhesive materials seems to play an important role in the ability to utilize the adhesive composition of matter as an effective sealant. The inventors of the present invention developed methods of applying the adhesive material that allow on-site curing of the adhesive and usage of bandages that form with the adhesive material an affective sealant especially for medical use.

SUMMARY OF THE INVENTION

It is an object of the present invention to provide novel phenol-based adhesives in order to further utilize them as adhesives and sealants.

It is another object of the present invention to provide various novel compositions of matter based on phenolic compounds to be used as adhesives for bio-medical applications.

It is yet another object of the present invention to provide methods of applying the adhesive material on-site, where tissue repair or tissue sealing is required so as to establish effective adhesive and sealing properties.

An additional object of the present invention is to provide a composition of matter for a pre-gel that is applied on a solid support to produce a sealing bandage.

It is therefore provided in accordance with a preferred embodiment of the present invention a composition of matter comprising:
- pre-gel that comprises at least one phenol-based compound, excluding phloroglucinol and its derivatives and at least one water miscible polymer;
- at least one cross linking agent capable of interacting with said at least one water miscible polymer.

Furthermore and in accordance with another preferred embodiment of the present invention, said at least one phenol-based compound can be in a form selected from monomer, non-cross linked polymer, or cross linked polymer.

Furthermore and in accordance with another preferred embodiment of the present invention, the composition of matter further comprising at least one activating agent capable of promoting production of polymeric form of said at least one phenol-based compound.

Furthermore and in accordance with another preferred embodiment of the present invention, said at least one activating agent is selected from a group of such as haloperoxidase (HPO) enzyme, an oxidizer, a halogen salt, and combinations thereof.

Furthermore and in accordance with another preferred embodiment of the present invention, said at least one water miscible polymer is naturally existing form or a synthetically prepared form of carbohydrate.

Furthermore and in accordance with another preferred embodiment of the present invention, said carbohydrate is selected from a group of carbohydrates consisting of alginic acid or salt from alginic acid.

Furthermore and in accordance with another preferred embodiment of the present invention, said at least one cross linking agent are multivalent charged materials such as polyelectrolytes, organic salts, and other inorganic salts.

Furthermore and in accordance with another preferred embodiment of the present invention, said multivalent charged materials are divalent ions.

Furthermore and in accordance with another preferred embodiment of the present invention, said divalent ions are selected from a group consisting of divalent ions such as divalent calcium ions (Ca+2) supplied, for example, by calcium chloride (CaCl2), or by a combination of calcium carbonate (CaCO3) and glucono-δ-lactone (GDL).

Furthermore and in accordance with another preferred embodiment of the present invention, said at least one phenol-based compound is selected from a group consisting of Gallic acid, Morin, Naringenin, Epicatechin, Catechin, Epigallocatechin, Gallocatechin, Epigallocatechin gallate, Epicatechin gallate.

Furthermore and in accordance with another preferred embodiment of the present invention, the composition of matter is supported on a support so as to form a bandage.

Furthermore and in accordance with another preferred embodiment of the present invention, said solid support is a thin film selected from a group of supports such as plastic, knitted mesh of fabric made from synthetic or natural polymer, gauze prepared form oxidized cellulose.

Furthermore and in accordance with another preferred embodiment of the present invention, said at least one cross linking agent is provided within said solid support.

Furthermore and in accordance with another preferred embodiment of the present invention, the composition of matter further comprising therapeutic materials such as drugs, growth factors, hormones, or any other therapeutic agent.

It is also provided in accordance with another embodiment of the present invention, a method of in-situ adhering comprising:
- providing pre-gel that comprises a mixture of at least one phenol-based compound and at least one water miscible polymer;
- spreading a layer of said pre-gel onto a surface;
- adding cross linking agent to said pre-gel;
- allowing said pre-gel to cure and adhere onto the surface.

Furthermore and in accordance with another preferred embodiment of the present invention, said adding cross linking agent is achieved by a method such as spraying, dripping, or wetting.

Furthermore and in accordance with another preferred embodiment of the present invention, the composition of matter further comprising adding an acid such as slowly hydrolyzing D-gluco-δ-lactone and wherein said cross linking agent is an insoluble salt and wherein said adding cross linking agent is achieved by blending.

Furthermore and in accordance with another preferred embodiment of the present invention, the composition of matter further comprising drying said pre-gel.

Furthermore and in accordance with another preferred embodiment of the present invention, the composition of matter further comprising drying said pre-gel with said cross linking agent.

Furthermore and in accordance with another preferred embodiment of the present invention, said at least one phenol-based compound can be in a form selected from monomer, non-cross linked polymer, or cross linked polymer.

Furthermore and in accordance with another preferred embodiment of the present invention, the composition of matter further comprising at least one activating agent capable of promoting production of polymeric form of said at least one phenol-based compound.

Furthermore and in accordance with another preferred embodiment of the present invention, said at least one activating agent is selected from a group of such as haloperoxidase (HPO) enzyme, an oxidizer, a halogen salt, and combinations thereof.

Furthermore and in accordance with another preferred embodiment of the present invention, said at least one water miscible polymer is naturally existing form or a synthetically prepared form of carbohydrate.

Furthermore and in accordance with another preferred embodiment of the present invention, said carbohydrate is selected from a group of carbohydrates consisting of alginic acid or salt from alginic acid.

Furthermore and in accordance with another preferred embodiment of the present invention, said at least one cross linking agent are multivalent charged materials such as polyelectrolytes, organic salts, and other inorganic salts.

Furthermore and in accordance with another preferred embodiment of the present invention, said multivalent charged materials are divalent ions.

Furthermore and in accordance with another preferred embodiment of the present invention, said divalent ions are selected from a group consisting of divalent ions such as divalent calcium ions ($Ca^{+2}$) supplied, for example, by calcium chloride ($CaCl_2$), or by a combination of calcium carbonate ($CaCO_3$) and gluconoδ-lactone (GDL).

Furthermore and in accordance with another preferred embodiment of the present invention, said at least one phenol-based compound is selected from a group consisting of Gallic acid, Morin, Naringenin, Epicatechin, Catechin, Epigallocatechin, Gallocatechin, Epigallocatechin gallate, Epicatechin gallate.

Furthermore and in accordance with another preferred embodiment of the present invention, said surface is a surface selected from a group of tissue, graft, or organ.

It is further provided in accordance with another preferred embodiment of the present invention, a use of the composition of matter as an adhesive.

Furthermore and in accordance with another preferred embodiment of the present invention, said adhesive is usable under dry or wet conditions.

Furthermore and in accordance with another preferred embodiment of the present invention, said adhesive is usable under dry conditions, for adhering a first surface to a second surface, wherein each of said first surface and said second surface is dry.

Furthermore and in accordance with another preferred embodiment of the present invention, said adhesive is usable under wet conditions, for adhering a first surface to a second surface, wherein at least one of said first surface and said second surface is wet.

Furthermore and in accordance with another preferred embodiment of the present invention, at least one of said first surface and said second surface is a body part or a component thereof, of a human or animal subject.

Furthermore and in accordance with another preferred embodiment of the present invention, said component is a tissue.

Furthermore and in accordance with another preferred embodiment of the present invention, said adhesive is usable as a sealant or sealing agent, for sealing or closing an opening in a surface.

Furthermore and in accordance with another preferred embodiment of the present invention, said sealing or closing takes place under dry or wet conditions.

Furthermore and in accordance with another preferred embodiment of the present invention, said surface having said opening is a body part or a component thereof, of a human or animal subject.

Furthermore and in accordance with another preferred embodiment of the present invention, said component is a tissue.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings.

DETAILED DESCRIPTION OF THE INVENTION AND THE FIGURES

Figure 1:
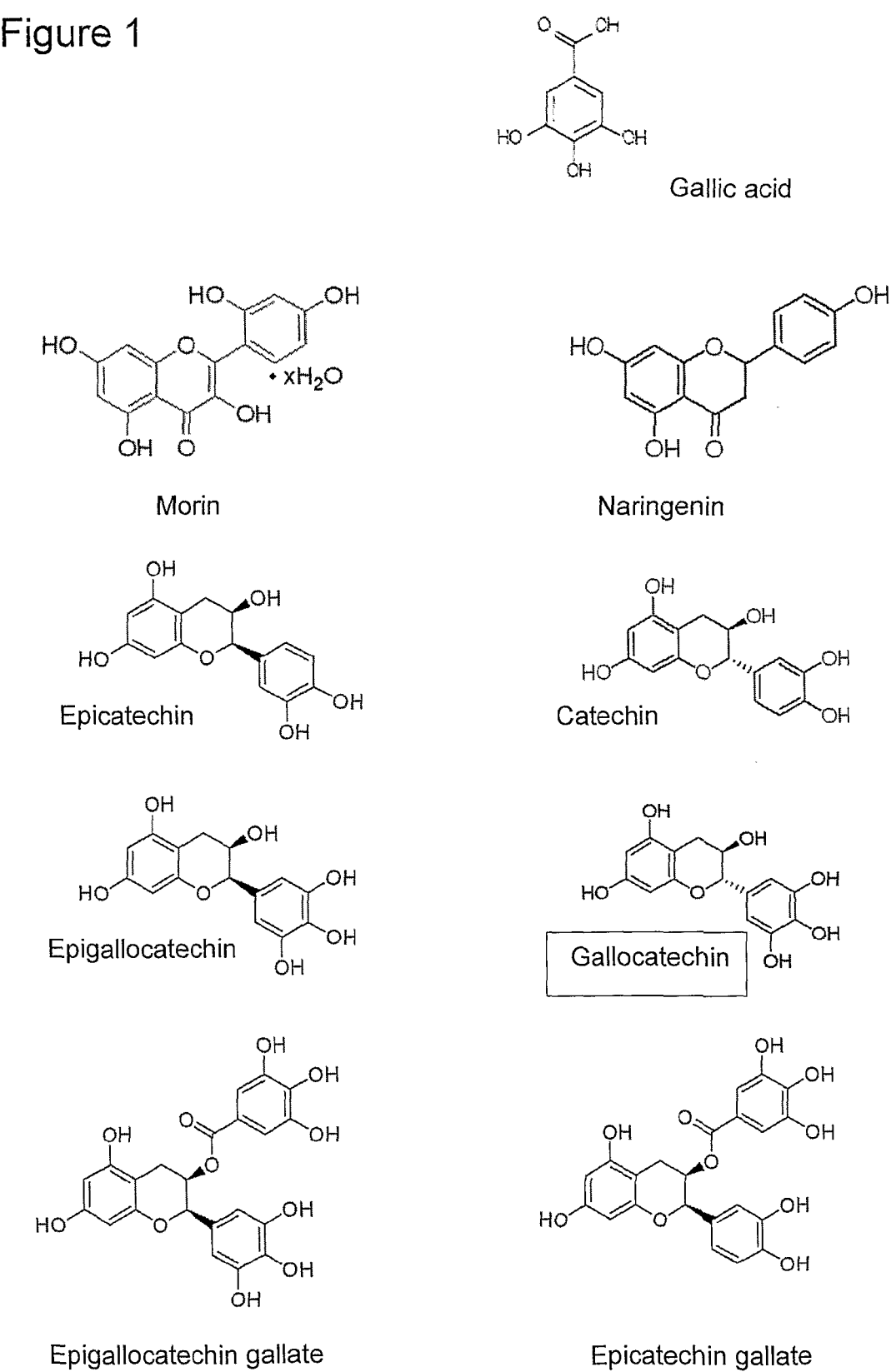
FIG. 1 illustrates several chemical structures of selected phenols that can be utilized as adhesive base materials, in their monomeric or polymeric forms.

The present invention provides novel composition-of-matter of adhesives and methods of applying thereof in a wide variety of different fields, and in particular, in the health care fields of medicine, dentistry, and veterinary science. The present invention is especially applicable for use by health care providers, such as medical, dental, and veterinary, surgeons, in procedures for reattaching or repairing body parts or components thereof, such as tissues of human or animal subjects, especially under wet conditions, but not necessarily. The composition-of-matter of the present invention, applied as an adhesive, may also function, and be usable, as a sealant or sealing agent, for sealing or closing an opening in a surface, for example, for preventing flow of liquid or/and gaseous fluid. Such a sealant or sealing agent can be used in a wide variety of applications, for example, for sealing or closing an opening in a medical device, of an aquarium, or of a wide variety of other objects or entities.

A main aspect of the present invention is providing a composition of matter that comprises at least one cross-linked form of a water miscible polymer and at least one phenol-based material. The phenol-based material can be in its monomeric or polymeric form.

Accordingly and optionally, at least one activating agent is used in the composition for promoting reaction and possible cross-linking, or/and oxidation, or/and some other modification, of any of the phenol type compound so as to produce its polymeric form. Such activating agents are, for example, haloperoxidase (HPO) enzyme, an oxidizer, a halogen salt, and combinations thereof.

The water miscible polymer is essentially any type or kind of naturally existing polymer or synthetically prepared polymer which is miscible in water. Examplary water miscible polymers can be naturally existing, or synthetically prepared, form of a carbohydrate (polysaccharide), such as alginic acid, or/and alginic acid itself. More preferably, the water miscible polymer is a naturally existing, or synthetically prepared, salt form of a carbohydrate (polysaccharide), such as a salt form of alginic acid, being an alginate. The water miscible polymer is in a cross-linked form. For an embodiment of the composition-of-matter of the present invention, wherein the water miscible polymer is an alginate, or alginic acid, preferably, the alginate, or the alginic acid, is cross-linked via interaction with divalent ions, for example, divalent calcium ions ($Ca^{+2}$)

supplied, for example, by calcium chloride ($CaCl_2$), or by a combination of calcium carbonate ($CaCO_3$) and glucono-δ-lactone (GDL).

Another main aspect of the present invention is providing a pre-gel that may be usable as an adhesive in combination with a solid support. The combined pre-gel and solid support may be functional and usable as a sealant or sealing agent, for sealing or closing an opening in a surface so as to prevent as an example flow of a fluid through the sealed or closed portion of the surface. The sealing or closing may take place under dry or wet conditions.

Reference is made to FIG. 1 illustrating several chemical structures of selected phenols that can be utilized as adhesive base materials. The structures are shown in their monomeric form, however, their polymeric form is being used also. These examples are of non-toxic polyphenols can be utilized as base material for an adhesive that can be used in the medical field. The exemplary polyphenols shown in FIG. 1 are appropriate analogues that can replace the natural components of glues such as "fucus glue" or others that were mentioned in the background section of this document. Most importantly, such commercially available polyphenols are purchased from Sigma as well as other manufacturers. A large selection of polyphenols was exploited in order to evaluate the influence of their molecular parameters (molecular weight, abundance of phenolic groups within the structure, molecular flexibility) on the interactions with the carbohydrate on one hand, and on the properties and the performance of the adhesive material, on the other.

It should be noted that some polyphenols are only sparingly soluble in water; however preliminary experience has shown that occasionally the solubility in polysaccharide solutions is higher compared to water.

One example for a polysaccharide that is included in the preparation of the adhesive material of the present invention is a commercial alginate supplied by FMC Biopolymer. Alginate is structured as a block copolymer with blocks of α-L-gluronic acid (G) and β-D-mannuronic acid (M) alternating interrupted by regions of more random distribution of M and G units. Sizes of the three blocks can vary over a wide range, giving rise to alginates of different properties. Two types of sodium alginate, Protanal LF 200 S with G content of ~70% and Protanal HF 120 RBS with G content of ~50% were used. It should be noted again that this alginate was used as an exemplary alginate and any other miscible polymer can be used in order to prepare the adhesive material.

Alternatively and optionally, alginate can be replaced with a polysaccharide that can undergo gelation upon interaction with ions and changes in temperature. In this case, the gels are dense cross-linked polymeric matrices that can hinder solute diffusion. Therefore drugs, growth factors, hormones, or any other therapeutic agents, can be entrapped within the cured glue or sealant and will be slowly released in the site of application.

In the specific case of alginate, gelation is induced by the addition of multivalent ions. For example, calcium ions were added either as $CaCl_2$, or by blending the mixture with insoluble salt such as $CaCO_3$ or CaEGTA followed by addition of the slowly hydrolyzing D-gluco-δ-lactone (GDL). Salts, which were previously shown to alter alginate-polyphenol complexation[31], were added to some of the formulations. Optionally, other sources of multivalent ions are polyelectrolytes, organic salts, and other inorganic salts (e.g. Al, Ba).

As mentioned herein before, the method of applying the adhesive material is one of the main aspects of the present invention and special focus is given to combining solid support to the adhesive material so as to form an adhering bandage. In the following text, the term "pre-gel" refers to a composition of matter that typically contains a polysaccharide such as alginate, polyphenol, salt and water, at any given ratios. The pre-gel may also contain multivalent ions, yet it has relatively low viscosity since the polysaccharide is not fully gelled. The solid support may be a thin film made from plastic (e.g. PGA, poly(caprolacton) etc.), knitted mesh of fabric made from synthetic or natural polymer, gauze prepared form oxidized cellulose etc. Any other composition of the pre-gel as claimed in the present invention can be used without limiting the scope of the present invention.

Optionally, the pre-gel glue may contain non-soluble suspended solids in the form of particles, fibers etc. which are added to enhance the mechanical strength of the glue.

The pre-gel glue is cured (solidified) so as to form an adhesive material typically due to the addition of multivalent ions or another method which induces polysaccharide gelation.

Several methods are used to apply the glue on site that requires tissue repair or tissue sealing as follows:
(1) Spreading a layer of the pre-gel on the tissue or surface followed by hardening (curing) of the polysaccharide which can be achieved, for example, by spraying, dripping, or wetting the pre-gel with an aqueous solution containing multivalent ions.
(2) Blending the pre-gel solution with insoluble salt of multivalent ions (e.g. $CaCO_3$ or CaEGTA) and an acid (e.g. the slowly hydrolyzing D-gluco-δ-lactone (GDL)), then spreading a layer on the tissue or the surface. The pre-gel hardens with time due to the slow dissolution of the multivalent salt.
(3) Providing a patch for solid support such as a thin film made from plastic (e.g. PGA, poly(caprolacton) etc.), knitted mesh of fabric made from synthetic or natural polymer, gauze prepared from oxidized cellulose etc. The patch or solid support is soaked with a pre-gel and placed on the tissue. Alternatively, a layer of pre-gel is spread on the tissue or the surface and the solid support is embedded within it.
Finally, the polysaccharide is hardened by spraying, dripping, or wetting the pre-gel with an aqueous solution containing multivalent ions.
(4) Blending the pre-gel solution with insoluble salt of multivalent ions (e.g. $CaCO_3$ or CaEGTA) and an acid (e.g. slowly hydrolyzing D-gluco-d-lactone (GDL) or acetic acid). A patch or solid support such as a thin film made from plastic (e.g. PGA, poly(caprolacton) etc.), knitted mesh of fabric made from synthetic or natural polymer, gauze prepared from oxidized cellulose etc. is soaked with a the pre-gel and placed on the tissue or the surface. Alternatively, a layer of pre-gel is spread on the tissue and the solid support is embedded within it. The pre-gel hardens with time due to the slow dissolution of the multivalent salt.
(5) Coating a solid support such as a thin film made from plastic (e.g. PGA, poly(caprolacton) etc.), knitted mesh of fabric made from synthetic or natural polymer, gauze prepared from oxidized cellulose as an example with multivalent ions. A layer of pre-gel is spread on the tissue or the surface and the solid support is embedded in it. The pre-gel hardens with time due to the slow release of the multivalent salt from the solid support.
(6) Preparing a dry film made from the components of the pre-gel. Multivalent ions are used to coat a solid support as described above, and the solid film is attached on top of the dried pre-gel. Both films are placed on a hydrated tissue. The hydration of the films leads to their adhering to the tissue. At the same time, the pre-gel hardens with time due to the slow release of the multivalent salt from the solid support.

(7) Preparing a dry film made from the components of the pre-gel, with added multivalent ions in a dry form. The dry multivalent ions may be incorporated in the pre-gel formulation or as a different layer of the dry film (i.e. multilayer film). The film is placed on a hydrated tissue or surface. The hydration of the film leads to its adhering to the tissue. At the same time, the pre-gel hardens with time due to the slow dissolution release of the multivalent salt.

Regardless of the method by which the bandage was prepared, additional top layers (typically made of polymers) may be added to the finished bandage to provide extra mechanical support, provide an inert layer that will separate between the inner bandage layers and the surrounding environment etc. The additional layers, by no means, limit the scope of the present invention.

In order to show the performance of the composition of matter of the present invention as adhesives, several adhesive properties were tested for several of the polyphenol-based adhesive materials and the adhesive bandage.

EXPERIMENTAL METHODS

Adhesive Properties

Adhesive strength is characterized using shear lap and tensile tests. The samples holders and specimens preparation was described in the inventor's PCT publication WO 06/092798. Briefly, two identical sample holders are used to prepare a specimen. The adhesive material is fixed to both sample holders using synthetic glue. Next, a measured volume of the studied composition of matter is applied onto one adherent, immediately covered with the other, clamped, and cured for a specified time period. Adhesion tests are performed using a Lloyd tensile machine equipped with a 50N load cell. 10 specimens are prepared for each formulation and a statistical analysis is performed. From practical reasons, and following previous works, specimen preparation and adhesion assays are performed at room temperature with no attempt to simulate gluing under water.[2, 8] However, evaluation of the influence of curing in humid environment was established on the final results.

The adhesion to different well-defined clean test substrates (e.g. glass, metals, and different types of plastic) is characterized for the different composition of matters.

Additional adhesion assays were performed using tissues obtained from a local slaughterhouse. These provide better sense for the glue's ability to adhere to moist and flexible surfaces.

Rheological Measurements

Rheological measurements were conducted using a Rheometric Scientific ARES strain-controlled rheometer fitted with a 50-mm cone-and-plate fixture and equipped with anti-evaporator cover that prevents sample dehydration. Oscillatory shear experiments were performed within the linear viscoelastic regime, where the dynamic storage modulus (G') and loss modulus (G") are independent of the strain amplitude. Calculations are done using the RSI Orchestrator 6.5.1 software. The critical calcium concentration required to induced a sol-gel transition at a given composition of matter concentration are determined from the appearance of a power law of the dynamic moduli[35], as proposed by Winter and Chambon[36, 37]. Moduli exhibiting power law dependency on the frequency w of G' $\sim \omega^{1.5}$ and G" $\sim \omega^1$ are characteristic to a viscoelastic fluid according to the Rouse-Zimm theory. Above the gel point, G' becomes larger than G" with a plateau appearing in the G' vs. $\omega$ curve at the low frequency range.

Wetting Properties

Advancing contact angles of the liquids on the test surfaces are measured by a computerized contact angle analyzer (CAM200, KSV, Helsinki, Finland). A micro Hamilton syringe were used to create the drop on the surface and to continuously add liquid during the measurement. The surface tension of the aqueous solutions was measured by the ring method. The work of the adhesion $W_{adh}$ is calculated according to the Young-Dupré equation $W_{adh} = \gamma_{LV}(1+\theta)$[8]. The wetting properties of both polyphenol solution and polyphenol/alginate was studied.

Miscible Polymer/Polyphenol Interactions $^1$H NMR Spectroscopy: Comparing spectra obtained from the composition of matter solutions with spectra obtained from the individual components provide a qualitative indication to intramolecular interactions[24].

Equilibrium Dialysis was previously used to determine the extent of binding of polyphenols to macromolecules[26]. Binding assays include dialyzing 0.5 ml polyphenol solution, contained in a Spectra/Por® dialysis tubing (Spectrum Laboratories®, CA, USA) against stirred polysaccharide solution[38]. Once equilibrium is achieved, the polyphenol concentration in both cells is determined spectrophotometrically. The partition coefficient is calculated from a mass balance. A control experiment (dialysis against water) is used to ensure that polyphenol is not adsorbed by the cellulose membrane installed in the dialysis tube.

Isothermal Titration Calorimetry (ITC) is used to quantify the magnitude of the interactions between the polyphenols and the polysaccharides (alginate). ITC is a technique that allows studying the heat of interaction between two molecules. Often, a "ligand" is titrated to a solution of a "macromolecule", and the heat released upon their interaction, Q, is monitored over time. As the two elements interact, heat is released or absorbed in direct proportion to the amount of association/dissociation that occurs. When the ligand in the cell becomes saturated with added macromolecule, the heat signal diminishes until only the background heat of dilution is observed. ITC measurements were performed using a VP-ITC Microcalorimeter (Microcal Inc.). ITC experiments include injecting known amounts of polyphenol solution into an aqueous alginate solution. Appropriate reference experiments (injection of buffer into alginate and polyphenol dilution) are performed as well. The experimental data were analyzed using the software provided with the instrument, which calculates the binding constant from the slope of the heat vs. injected amount at the saturation point. In a case of small binding energies, one of the analysis scheme previously applied by the inventors of the present invention and others[39-41] was followed. Data obtained from ITC and equilibrium binding experiments can be further used to calculate the free energy and entropy of binding[26, 40]. This approach provides additional insight into the binding mechanism and in particular highlights the related importance of the entropy driven hydrophobic interactions and the enthalpy driven hydrogen bonding.

Nanostructure Characterization

Nanostructure characterization allows assessment of the estimated model of polyphenols and alginate that is hypnotized to form a nanocomposite material. Moreover, the structural parameters of such nanocomposite might have a significant impact on its properties.

SAXS measurements are mostly performed using a slit-collimated compact Kratky camera (A. Paar Co.) equipped with a linear position sensitive detector system (Raytech), with pulse-height discrimination and a multichannel analyzer (Nucleus). A total of 3000 or more counts for each channel are collected in order to obtain a high signal to noise ratio. Primary beam intensities is determined using the moving slit method[42] and subsequently using a thin quartz monitor as a secondary standard. The scattering curves, as a function of the scattering vector $q=4\pi \sin \theta/\lambda$ (where $2\theta$ and $\lambda$ are the scattering angle and the wavelength, respectively), are corrected for counting time and for sample absorption and the background is subtracted. Desmearing procedure is performed according to the Indirect Transformation Method[43] using the ITP program. Data analysis includes fitting the desmeared curve to an appropriate model using a least-squares procedure. As a starting point, the inventors fitted the model used for the algal-born glue[24], known as "broken rod linked by a flexible chain" model[44, 45]:

$$I(q) \propto S(q)P(q) \propto \underbrace{\frac{1}{1+C\exp(-\xi^2 q^2)}}_{S(q)} \underbrace{\frac{1}{q^2}\sum_i k_i q\left[\frac{J_1(qR_i)}{qR_i}\right]^2}_{P(q)}$$

Where P(q) is the form factor of cylindrical elements specified by cross-sectional radii $R_i$ and relative weights of $k_i$. The electrostatic interactions are taken into account by the structure factor S(q) that assumes a Gaussian-type interaction potential specified by the correlation length $\xi$ C is a an adjustable parameter representing the strength of interaction, which depends on the second virial coefficient and the polymer concentration.[44 45].

Cryo-Transmission Electron Microscopy (cryo-TEM) is used in parallel for direct visualization of the nanostructure. Ultra-fast cooled vitrified specimens, prepared at controlled conditions of 25° C. and 100% relative humidity as described elsewhere[46], are studied in a Philips CM120 cryo-TEM operating at 120 kV. An Oxford CT3500 cooling-holder system that keeps the specimens at about −180° C. was used. Low electron-dose imaging is performed with a Gatan Multiscan 791 CCD camera, using the Gatan Digital Micrograph 3.1 software package.

Pulsatile Flow System.

A flow system was built in order to serve as a model system that imitates the forces working on blood vessels in the human body, thus providing a more realistic method of testing the adhesives. The flow system creates pressure swing between the systolic and diastolic blood pressures. The inventors tested punctured aorta originated from bovine or swine as a substrate for testing.

In order to analyze the results, an experimental parameter named sealing ratio (SR) was defined as $$SR = 1 - \frac{\text{Flow through sealed hole}}{\text{Flow rate through unsealed hole}}.$$

T-Peel Test

T-peel test is based on ASTM F-2256-05 that was developed as testing method for surgical adhesives and sealants.

The samples used for the T-peel test are of constant dimensions.

The solid support dimensions are 150±1 mm length and 25±1 mm width. The dimensions of the sample tissue, which was an artery, equal to those of the solid support.

1.75 ml of adhesive was applied on the tissue. The hardening film is then applied and a weight of 1 kg is placed over it for one minute. The sample is then placed in the extension test machine and the test is conducted.

The results are analyzed as described in ASTM F-2256-05.

EXPERIMENTAL RESULTS

Figure 2:
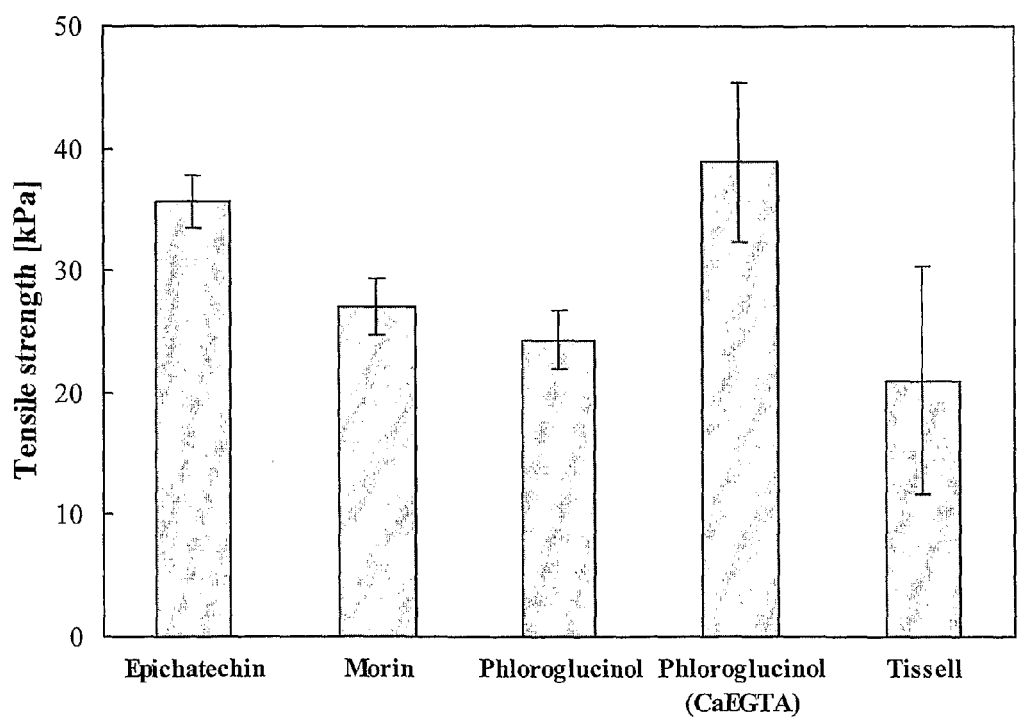
FIG. 2 illustrates tensile strength required to separate two porcine tissue strips adhered by polyphonel-based adhering materials in accordance with preferred embodiments of the present invention. The right bar represents the tensile strength obtained with Tisseel®, a commercial fibrin sealant.

Reference is now made to FIG. 2 illustrating tensile strength required to separate two porcine tissue strips adhered by polyphonel-based adhering materials in accordance with preferred embodiments of the present invention. The right bar represents the tensile strength obtained with Tisseel®, a commercial fibrin sealant, for comparison. Results show firm adhesion between the tissue surfaces after adherence of the tissues with a phenolic adhering material; wherein the tissues are porcine muscle tissues.

Different types of polyphenols were used to demonstrate the feasibility of the present invention. The composition of the different polyphenol-based adhesive materials shows significant adhesion properties. It should be noted that some of the polyphenol-based adhesive materials showed better adhesion to the tissue than Tisseel®, a commercial fibrin sealant.

Figure 3:
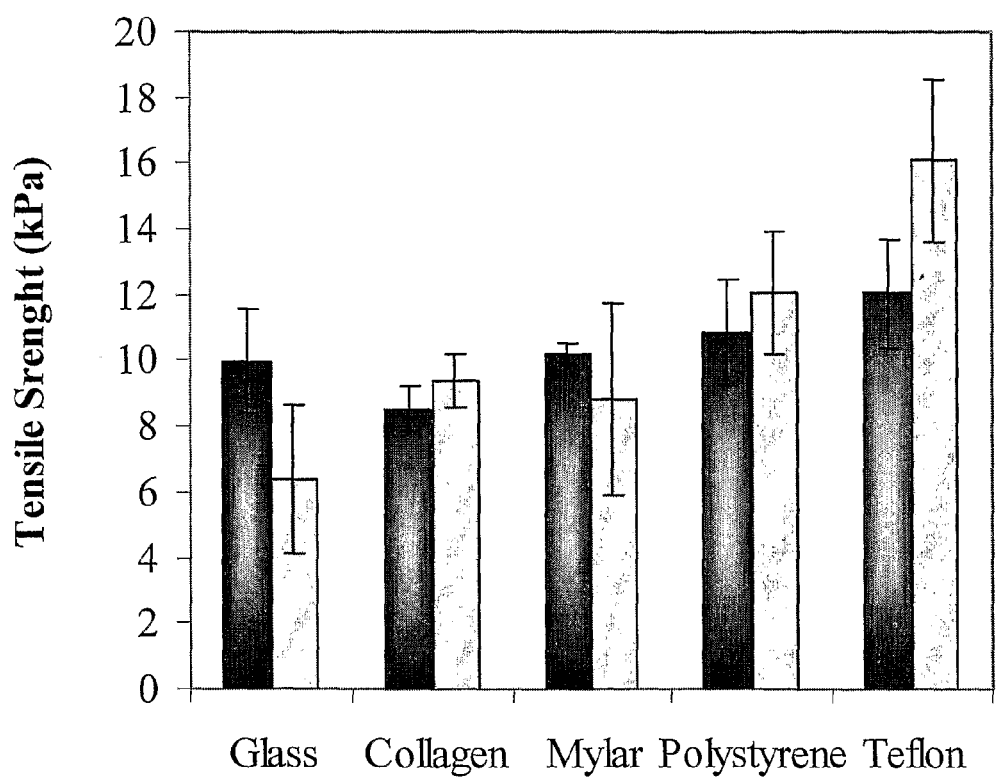
FIG. 3 illustrates tensile strength of KI-oxidized adhesive (dark grey) in accordance with a preferred embodiment of the present invention compared to KI-oxidized Fucus glue (light grey) to various substrates.

Reference is now made to FIG. 3 illustrating tensile strength of KI-oxidized adhesive (dark grey) in accordance with a preferred embodiment of the present invention compared to KI-oxidized Fucus glue (light grey) to various substrates. Tensile strength of alga-born glue, composed of components extracted from *Fucus Serratus* (15 mg/ml Alginate, 5 mg/ml polyphenol, 4 mM ca ions) are compared to these of a biomimetic composition in matter in which the algae polyphenol was replaced with phloroglucinol and the algae alginate with Protanal LF 200 S alginate. All samples were oxidized by adding 0.75 U/ml BPO, 0.44% $H_2O_2$ and 4.4 mg/ml KI. Oxidation was verified using NMR (data not shown). Samples were cured for 20 minutes. The adhesive strengths of the biomimetic adhesive was comparable to that of the alga-born one. Moreover, both glues seem to adhere better to the more hydrophobic surfaces.

Figure 4:
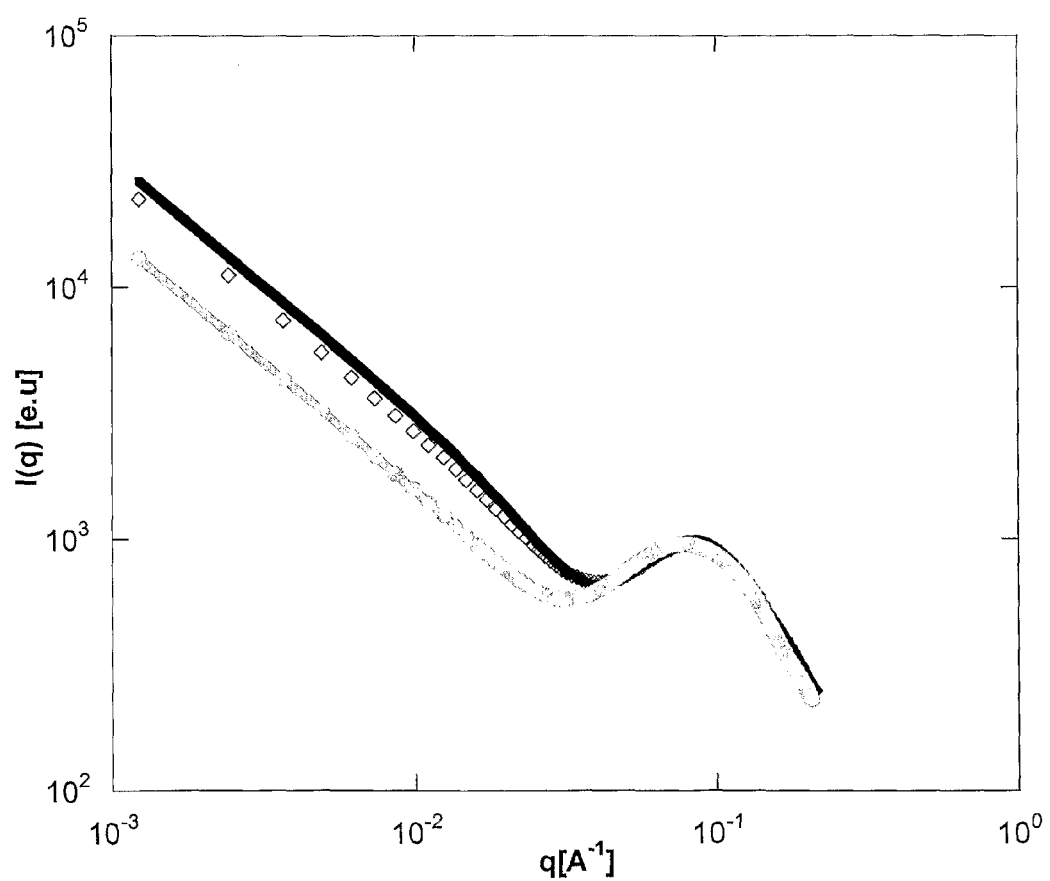
FIG. 4 illustrates SAXS curves from alginate and calcium (○) and phloroglucinol-containing adhesive material (◇). The solid lines represent the fit results of the "broken rod linked by a flexible chain" model. Best-fit parameters are: Alginate gel: $\xi=25$ Å, $R_1=8.2$ Å, $R_2=118$ Å, $C=8.1$. Biomimetic glue: $\xi=22$ Å, $R_1=7.8$ Å, $R_2=85$ Å, $C=6.7$.

Reference is now made to FIG. 4 illustrating SAXS curves from alginate (15 mg/ml) and calcium (4 mM) polyphenol, 0.75 U/ml BPO, 0.44% $H_2O_2$, 4.4 mg/ml KI, 15 mg/ml alginate and 4 mM calcium ions was (○) and phloroglucinol-containing adhesive material (alginate 15 mg/ml, phlologlucinol 5 mg/ml, Ca4 mM)(◇). The solid lines represent the fit results of the "broken rod linked by a flexible chain" model. Best-fit parameters are: Alginate gel: $\xi$=25 Å, $R_1$=8.2 Å, $R_2$=118 Å, C=8.1. Biomimetic glue: $\xi$=22 Å, $R_1$=7.8 Å, $R_2$=85 Å, C=6.7. The SAXS results comparison demonstrates the existence of alginate-phloroglucinol interactions in a biomimetic composition of matter. The overall structure of the glue resembles that of alginate gel. Yet, since the scattering from phloroglucinol by itself was very weak and a scattering curve could not be obtained, the differences between the two curves can be attributed to interactions between the alginate and the phloroglucinol. As in the case of algal-born glue[24], both curves were well fitted by the "broken rod linked by a flexible chain" model. The analysis of the SAXS data showed that the two samples differ by the correlation length $\xi$, the adjustable parameter C and $R_2$ that represents the alginates' tendency to form large aggregates[47]. Smaller correlation length and adjustable parameter were obtained for the biomimetic glue, thus indicating weaker electrostatic repulsion and lower hydrophilicity compared to alginate gel[48].

Figure 5:
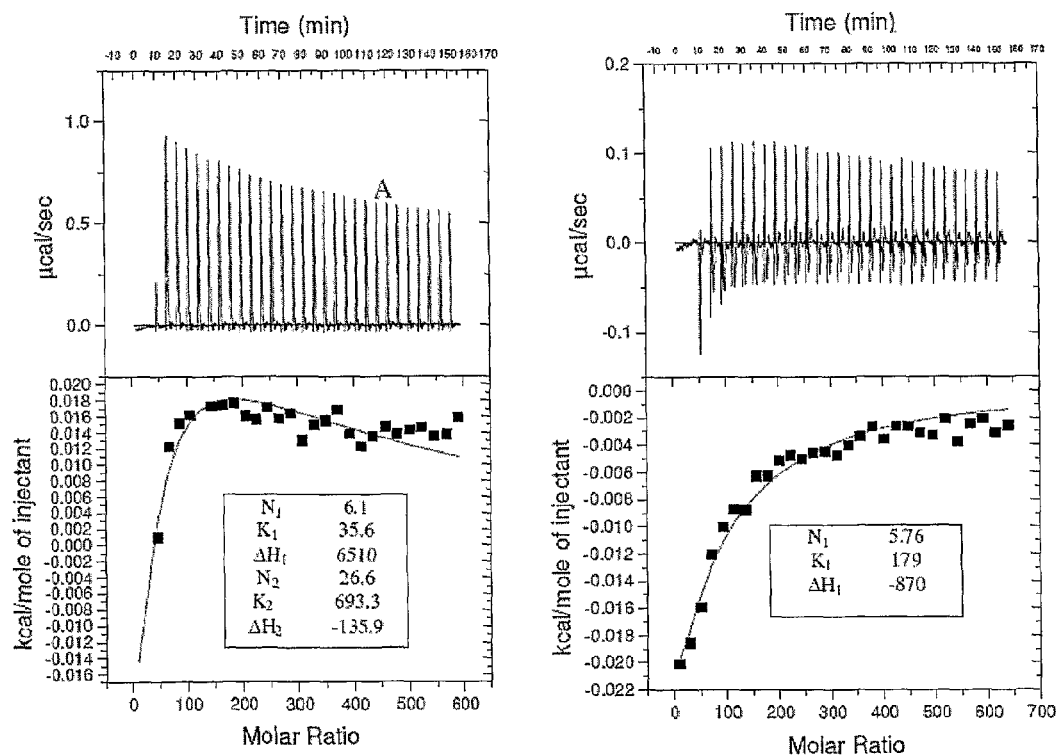
FIG. 5 illustrates ITC data for (A) Phloroglucinol (8 mg/ml, 63.4 mM) titrated into LF-200S alginate (5 mg/ml, 0.0236 mM). Lower plot shows a fit to a two-site model. (B) Epicatechin (2 mg/ml, 68.8 mM) titrated into LF-200S alginate (5 mg/ml, 0.0236 mM). Lower plot shows a fit to a one-site model.

Reference is now made to FIG. 5 illustrating ITC data for (A) Phloroglucinol (8 mg/ml, 63.4 mM) titrated into LF-200S alginate (5 mg/ml, 0.0236 mM). Lower plot shows a fit to a two-site model. (B) Epicatechin (2 mg/ml, 68.8 mM) titrated into LF-200S alginate (5 mg/ml, 0.0236 mM). Lower plot shows a fit to a one-site model. Two preliminary ITC measurements detected heat changes during injection of polyphenol into alginate solution, thus providing additional evidence to interactions between the two materials that comprises the adhesive material. Moreover, the affect of the polyphenol's molecular structure is evident from a comparison between the experiments.

As mentioned herein above, many different configurations of dry film may be used in order to apply the adhering material of the present invention with their formulations. The composition of matter of the adhering material can differ in their physical form, composition and preparation method. The following examples include two different preparation methods and two different compositions.

Air drier film, a solution containing 35 mg/ml alginate (LF200S), 10 mg/ml PHG and 1 mg/ml colorant was cast into molds with different depths and air dried for 24 hrs. The film was peeled and use in conjunction with ORC containing ~1 mg/cm$^2$ CaCl2 as hardener. The sealing ratio was measured using the flow system mentioned above. A sealing ratio close to 1 at 120 mmHg was achieved for 14 samples.

Freeze dried film are prepared from a solution containing alginate, PHG and colorant that were cast into molds with different widths. The solutions were freeze by liquid nitrogen, however, can be freeze also by solid carbon dioxide or any other cooling method. In some cases, a second layer was applied, wherein this layer contained PVA/PEG/CACl$_2$ mixture. The samples were than inserted into freeze drier until completely dried.

Single layer samples—these patches were used in conjunction with external ORC hardening system containing ~1 mg/cm2 CaCl$_2$. The solution used for casting these films contained 35 mg/ml alginate (LF200S), 10 mg/ml PHG and 0.3 mg/ml colorant (acid green 25 or other such as indigo carmine)

The sealing ratio for 1.5 mm thick film was approximately 1 at 200 mmHg, The number of repetitions was 22.

Multilayer samples—a first 1.5 mm thick layer was cast using solution containing 35 mg/ml alginate (LF200S), 10 mg/ml PHG and 0.3 mg/ml colorant (acid green 25 or other such as indigo carmine). After the first layer was frozen, a second layer was cast using a solution containing PVA/PEG/CaCl2 in the following concentrations, 34.4/15.6/20 mg/ml. Tthe second layer was allowed to freeze and the multilayer film was placed on freeze drier until completely dried. The sealing ratio for this composition was found to be approx. 1 at 200 mmHg.

Although most of the results shown herein deal with alginate as a preferred water miscible polymer, a carbohydrate, other water miscible polymers were tested. As an example, a T-peel test was conducted for polygalacturonic acid as another preferred carbohydrate that shows T-peel strength of 0.076N/cm.

For any of the above described preferred embodiments or formulations of the composition of matter of the present invention generally usable as an adhesive; the adhesive may be functional and usable as sealant or sealing agent, for sealing or closing an opening of a dry or wet surfaces. For example, for preventing flow of a liquid or/and gaseous fluid through the sealed or closed portion of the surface. Accordingly, the sealing or closing may take place under dry or wet conditions. The surface having the opening which is sealed or closed may be a body part or a component thereof (e.g. a tissue), of a human or animal subject. Such a sealant or sealing agent can be used in a wide variety of applications, for example, for sealing or closing an opening in a dry or wet body part, or in a dry or wet surface of a medical device, of an aquarium, or of a wide variety of other objects or entities.

Any of the above described preferred embodiments or formulations of the composition of matter of the present invention are generally usable as an adhesive, of a variety of different types of surfaces, under dry or wet conditions.

In particular, the composition of matter of the present invention is generally usable as an adhesive under dry conditions, for example, for adhering a first surface to a second surface, wherein both surfaces are dry. Alternatively and advantageously, the composition of matter of the present invention is generally usable as an adhesive under wet conditions, for example, for adhering a first surface to a second surface wherein the first surface is wet and/or the second surface is wet.

Any of the above described preferred embodiments or formulations of the composition of matter of the present invention is generally usable as a sealant or an adhesive in any condition, wet or dry, and on any kind of surface, in a wide variety of different fields such as health care, medicine, dentistry, veterinary, as well as other general fields such as commercial, laboratory or home use.

It should be clear that the description of the configurations and attached Figures set forth in this specification serves only for a better understanding of the invention, without limiting its scope as covered by the following Claims.

It should also be clear that after reading the present specification a skilled person, can make adjustments or amendments to the attached Figures and above described configurations that would still be covered by the following Claims.

REFERENCES (1) Webster, I.; West, P. J. "Adhesives for medical applications" In *Polymeric Biomaterials*, Dumitriu, S., Eds.; Marcel Dekker, Inc.: New York, 2002;

(2) Yu, M.; Deming, T. J. "*Synthetic Polypeptide Mimics of Marine Adhesives*" Macromolecules 1998, 31, 4739-4745.

(3) Callow, M., E.; Callow, J., E. "*Marine biofouling: a sticky problem*" Biologist (London, England) 2002, 49, 10-14.

(4) Hwang, D. S.; Yoo, H. J.; Jun, J. H.; Moon, W. K.; Cha, H. J. "*Expression of functional recombinant mussel adhesive protein Mgfp-5* in *Escherichia coli*" Appl. Environ. Microbiol. 2004, 70, 3352-3359.

(5) Waite, J. H. "*Nature's underwater adhesive specialist*" International Journal of Adhesion and Adhesives 1987, 7, 9-14.

(6) Waite, J. H. "*Reverse engineering of bioadhesion in marine mussels*" Ann. N.Y. Acad. Sci. 1999, 875, 301-309.

(7) Vreeland, V.; Waite, J. H.; Epstein, L. "*Polyphenols and oxidases in substratum adhesion by marine algae and mussels*" Journal of Phycology 1998, 34, 1-8.

(8) Yamamoto, H.; Sakai, Y.; Ohkawa, K. "*Synthesis and wettability characteristics of model adhesive protein sequences inspired by a marine mussel*" Biomacromolecules 2000, 1, 543-551.

(9) Ohkawa, K.; Ichimiya, K.; Nishida, A.; Yamamoto, H. "*Synthesis and surface chemical properties of adhesive protein of the asian freshwater mussel, Limnoperna fortunei*" Macromolecular Bioscience 2001, 1, 376-386.

(10) Tatehata, H.; Mochizuki, A.; Kawashima, T.; Yamashita, S.; Ohkawa, K.; Yamamoto, H. "*Oxidative reaction and conformational studies on synthetic sequential polypeptides of mussel adhesive proteins*" Current Trends in Polymer Science 2000, 5, 91-96.

(11) Tatehata, H.; Mochizuki, A.; Kawashima, T.; Yamashita, S.; Yamamoto, H. "*Model polypeptide of mussel adhesive* protein. I. Synthesis and adhesive studies of sequential polypeptides (X-Tyr-Lys)n and (Y-Lys)n" *J. Appl. Polym. Sci.* 2000, 76, 929-937.

(12) Yamamoto, H.; Nishida, A.; Ohkawa, K. "*Wettability and adhesion of marine and related adhesive proteins*" *Colloids and Surfaces, A: Physicochemical and Engineering Aspects* 1999, 149, 553-559.

(13) Yamamoto, H.; Ogawa, T.; Nishida, A. "*Molecular weight dependence of wettability and molecular adsorption of poly-L-lysine at the air-water interface*" *J. Colloid Interface Sci.* 1995, 176, 105-110.

(14) Wang, J.; Liu, C.; Lu, X.; Yin, M. "*Co-polypeptides of 3,4-dihydroxyphenylalanine and -lysine to mimic marine adhesive protein*" *Biomaterials* 2007, 28, 3456-3468.

(15) Lee, B. P.; Dalsin, J. L.; Messersmith, P. B. "*Synthesis and Gelation of DOPA-Modified Poly(ethylene glycol) Hydrogels*" *Biomacromolecules* 2002, 3, 1038-1047.

(16) Lee, B. P.; Huang, K.; Nunalee, F. N.; Shull, K. R.; Messersmith, P. B. "*Synthesis of 3,4-dihydroxyphenylalanine (DOPA) containing monomers and their co-polymerization with PEG-diacrylate to form hydrogels*" *J. Biomater. Sci. Polym. Ed.* 2004, 15, 449-464.

(17) Catron, N. D.; Lee, H.; Messersmith, P. B. "*Enhancement of poly(ethylene glycol) mucoadsorption by biomimetic end group functionalization*" *Biointerphases* 2006, 1, 134-141.

(18) Messersmith, P. B. "*Mussel adhesive protein mimetics: polymer-peptide bioconjugates for tissue adhesion and antifouling surfaces*" *PMSE Preprints* 2006, 94, 129.

(19) Huang, K.; Lee, B.; Messersmith, P. B. "*Synthesis and characterization of self-assembling block copolymers containing adhesive moieties*" *Polym. Prepr. (Am. Chem. Soc., Div. Polym. Chem.)* 2001, 42, 147-148.

(20) Westwood, G.; Horton, T. N.; Wilker, J. J. "*Simplified Polymer Mimics of Cross-Linking Adhesive Proteins*" *Macromolecules* (Washington, D.C., United States) 2007, 40, 3960-3964.

(21) Vreeland, V.; Epstein, L. "*Analysis of plant-substratum adhesives*" *Modern Methods of Plant Analysis* 1996, 17, 95-116.

(22) Berglin, M.; Delage, L.; Potin, P.; Vilter, H.; Elwing, H. "*Enzymatic Cross-Linking of a Phenolic Polymer Extracted from the Marine Alga Fucus serratus*" *Biomacromolecules* 2004, 5, 2376-2383.

(23) Bitton, R. "*The Influence of Halide-Mediated Oxidation on Algae-Born Adhesives*" *Macromolecular Bioscience* 2007, In press,

(24) Bitton, R.; Ben-Yehuda, M.; Davidovich, M.; Balazs, Y.; Potin, P.; Delage, L.; Colin, C.; Bianco-Peled, H. "*Structure of algal-born phenolic polymeric adhesives*" *Macromolecular Bioscience* 2006, 6, 737-746.

(25) Cai, Y.; Gaffney, S. H.; Lilley, T. H.; Magnolato, D.; Martin, R.; Spencer, C. M.; Haslam, E. "*Polyphenol interactions. Part 4. Model studies with caffeine and cyclodextrins*" Journal of the Chemical Society, Perkin Transactions 2: *Physical Organic Chemistry (1972-1999)* 1990, 2197-2209.

(26) McManus, J. P.; Davis, K. G.; Beart, J. E.; Gaffney, S. H.; Lilley, T. H.; Haslam, E. "*Polyphenol interactions. Part 1. Introduction: some observations on the reversible complexation of polyphenols with proteins and polysaccharides*" *Journal of the Chemical Society, Perkin Transactions 2: Physical Organic Chemistry (1972-1999)* 1985, 1429-1438.

(27) Gaffney, S. H.; Martin, R.; Lilley, T. H.; Haslam, E.; Magnolato, D. "*The association of polyphenols with caffeine and a-and b-cyclodextrin in aqueous media*" *J. Chem, Soc., Chem. Commun.* 1986, 107-109.

(28) Renard, C. M. G. C.; Baron, A.; Guyot, S.; Drilleau, J. F. "*Interactions between apple cell walls and native apple polyphenols: quantification and some consequences*" *Int. J. Biol. Macromol.* 2001, 29, 115-125.

(29) Bourvellec, C. L.; Bouchet, B.; Renard, C. M. G. C. "*Non-covalent interaction between procyanidins and apple cell wall material. Part III: Study on model polysaccharides*" *Biochim. Biophys. Acta* 2005, 1725, 10-18.

(30) Nishinari, K.; Kim, B.; Fang, Y.; Nitta, Y.; Takemasa, M. "*Rheological and related study of gelation of xyloglucan in the presence of small molecules and other polysaccharides*" *Cellulose* (Dordrecht, Netherlands) 2006, 13, 365-374.

(31) Haslam, E.; Lilley, T. H.; Warminski, E.; Liao, H.; Cai, Y.; Martin, R.; Gaffney, S. H.; Goulding, P. N.; Luck, G. "*Polyphenol complexation. A study in molecular recognition*" In *Phenolic Compounds in Foods and Their Effects on Health I, Analysis, Occurrence & Chemistry*, Ho, C.-T.; Lee, C. Y.; Huang, M.-T., Eds.; American Chemical Society: Washington, D.C., 1992; 506.

(32) Sklenar, V.; Piotto, M.; Leppik, R.; Saudek, V. "*Gradient-tailored water suppression for proton-nitrogen-15 HSQC experiments optimized to retain full sensitivity*" *Journal of Magnetic Resonance, Series A* 1993, 102, 241-245.

(33) Piotto, M.; Saudek, V.; Sklenar, V. "*Gradient-tailored excitation for single-quantum NMR spectroscopy of aqueous solutions*" *J. Biomol. NMR* 1992, 2, 661-665.

(34) Manderville, R. A. "*Ambident reactivity of phenoxyl radicals in DNA adduction*" *Can. J. Chem.* 2005, 83, 1261-1267.

(35) Liu, X.; Qian, L.; Shu, T.; Tong, Z. "*Rheology characterization of sol-gel transition in aqueous alginate solutions induced by calcium cations through in situ release*" *Polymer* 2002, 44, 407-412.

(36) Chambon, F.; Winter, H. H. "*Linear viscoelasticity at the gel point of a crosslinking PDMS with imbalanced stoichiometry*" *Journal of Rheology* (New York, N.Y., United States) 1987, 31, 683-697.

(37) Winter, H. H.; Chambon, F. "*Analysis of linear viscoelasticity of a crosslinking polymer at the gel point*" *Journal of Rheology* (New York, N.Y., United States) 1986, 30, 367-382.

(38) Regev, R.; Yeheskely-Hayon, D.; Katzir, H.; Eytan, G. D. "*Transport of anthracyclines and mitoxantrone across membranes by a flip-flop mechanism*" Biochem. Pharmacol. 2005, 70, 161-169.

(39) Kimhi, 0.; Bianco-Peled, H. "*Study of the Interactions between Protein-Imprinted Hydrogels and Their Templates*" *Langmuir* 2007, 23, 6329-6335.

(40) Bianco-Peled, H.; Gryc, S. "*Binding of Amino Acids to \"Smart\" Sorbents: Where Does Hydrophobicity Come into Play?*" *Langmuir* 2004, 20, 169-174.

(41) Kimhi, O.; Bianco-Peled, H. "*Microcalorimetry Study of the Interactions between Poly(N-isopropylacrylamide) Microgels and Amino Acids*" *Langmuir* 2002, 18, 8587-8592.

(42) Stabinger, H.; Kratky, O. "*A new technique for the measurement of the absolute intensity of x-ray small angle scattering. The moving slit method*" *Makromol. Chem.* 1978, 179, 1655-1659.

(43) Glatter, O. "*A New Method for the Evaluation of Small-Angle Scattering Data*" *j.Appl.Cryst* 1977, 10, 415-421.

(44) Yuguchi, Y.; Urakawa, H.; Kajiwara, K.; Draget, K. I.; Stokke, B. T. "*Small-angle x-ray scattering and rheologi-*

(45) Yuguchi, Y.; Mimura, M.; Urakawa, H.; Kitamura, S.; Ohno, S.; Kajiwara, K. "*Small angle x-ray characterization of gellan gum containing a high content of sodium in aqueous solution*" Carbohydr. Polym. 1996, 30, 83-93.

(46) Bellare, J. R.; Davis, H. T.; Scriven, L. E.; Talmon, Y. "*Controlled environment vitrification system: an improved sample preparation technique*" J. Electron Microsc. Tech. 1988, 10, 87-111.

(47) Windhues, T.; Borchard, W. "*Effect of acetylation on physico-chemical properties of bacterial and algal alginates in physiological sodium chloride solutions investigated with light scattering techniques*" Carbohydr. Polym. 2003, 52, 47-52.

(48) Shimode, M.; Mimura, M.; Urakawa, H.; Yamanaka, S.; Kajiwara, K. "*Dye aggregation observed by small-angle x-ray scatterings. Part 2. Interaction between the dye aggregates in aqueous solution*" Sen'i Gakkaishi 1996, 52, 301-309.

The invention claimed is:

1. A composition of matter, comprising:
a non-protein based pre-gel that comprises
at least one phenol-based compound, excluding phloroglucinol and its derivatives,
at least one water miscible polymer selected from the group consisting of a naturally existing form of a carbohydrate, a synthetically prepared form of carbohydrate, and a salt of an anionic polysaccharide, and
at least one cross linking agent capable of interacting with said at least one water miscible polymer.

2. The composition of matter as claimed in claim 1, wherein said at least one phenol-based compound is in a form selected from at least one of monomer, non-cross linked polymer, or cross linked polymer.

3. The composition of matter as claimed in claim 1, further comprising at least one activating agent capable of promoting production of the polymeric form of said at least one phenol-based compound.

4. The composition of matter as claimed in claim 3, wherein said at least one activating agent is selected from the group consisting of haloperoxidase (HPO) enzyme, an oxidizer, a halogen salt, and combinations thereof.

5. The composition of matter as claimed in claim 1, wherein said water miscible polymer is selected from at least one member of the group consisting of alginic acid, polygalacturonic acid and an alginic acid salt.

6. A method of in-situ adhering, comprising:
providing a non-protein based pre-gel that comprises a mixture of at least one phenol-based compound, excluding phloroglucinol and its derivatives, and at least one water miscible polymer selected from the group consisting of a naturally existing form of a carbohydrate, a synthetically prepared form of carbohydrate, and a salt of an anionic polysaccharide;
spreading a layer of said pre-gel onto a first surface;
adding cross linking agent to said pre-gel; and
allowing said pre-gel to cure and adhere onto the first surface.

7. The method as claimed in claim 6, wherein said step of adding cross linking agent is achieved by spraying, dripping, or wetting.

8. The method as claimed in claim 6, further comprising adding an acid by slowly hydrolyzing D-gluco-δ-lactone and wherein said cross linking agent is an insoluble salt and wherein said step of adding cross linking agent is achieved by blending.

9. The method as claimed in claim 6, further comprising drying said pre-gel.

10. The method as claimed in claim 6, further comprising drying said pre-gel with said cross linking agent.

11. The method as claimed in claim 6, wherein said first surface is a surface of a tissue, of a graft, or of an organ.

12. The method of claim 6, further comprising adhering the first surface to a second surface, wherein each of said first surface and said second surface is dry.

13. The method of claim 6, further comprising adhering the first surface to a second surface, wherein at least one of said first surface and said second surface is wet.

14. The method of claim 6, wherein the first surface has an opening and further comprising closing the opening in the first surface.

15. The method of claim 11, wherein said first surface has an opening and wherein said step of
allowing said pre-gel to cure and adhere onto the first surface causes the closing of the opening in the first surface.

16. The method of claim 11, further including the step of adhering the first surface to a second surface.

17. The method as claimed in claim 6, wherein said at least one cross linking agent is a multivalent charged material selected from the group consisting of polyelectrolytes, organic salts, and inorganic salts.

18. The method as claimed in claim 17, wherein said multivalent charged material is at least one divalent ion.

19. The method as claimed in claim 18, wherein said divalent ion is a calcium ion ($Ca^2$).

20. The composition of matter as claimed in claim 1, wherein said at least one phenol-based compound is at least one member selected from the group consisting of Gallic acid, Morin, Naringenin, Epicatechin, Catechin, Epigallocatechin, Gallocatechin, Epigallocatechin gallate, and Epicatechin gallate.

21. The composition of matter as claimed in claim 1, further comprising therapeutic materials selected from the group consisting of drugs, growth factors and hormones.

* * * * *